(12) United States Patent
Ellis

(10) Patent No.: US 6,342,199 B1
(45) Date of Patent: Jan. 29, 2002

(54) METHOD FOR CARRYING OUT REACTIONS CHARACTERIZED BY AN EQUILIBRIUM

(76) Inventor: Vincent Simon Ellis, Schutterlaan, B-3078 Everberg (BE)

( * ) Notice: Subject to any disclaimer, the term of this patent is extended or adjusted under 35 U.S.C. 154(b) by 0 days.

(21) Appl. No.: 09/284,464
(22) PCT Filed: Oct. 8, 1997
(86) PCT No.: PCT/EP97/05542
§ 371 Date: Jun. 18, 1999
§ 102(e) Date: Jun. 18, 1999
(87) PCT Pub. No.: WO98/17381
PCT Pub. Date: Apr. 30, 1998

(30) Foreign Application Priority Data

Oct. 18, 1996 (DE) .......................... 196 43 165

(51) Int. Cl.$^7$ .......................... C07C 67/02; C07C 51/00
(52) U.S. Cl. .................. 423/659; 554/170; 554/172; 554/173; 560/234; 568/679
(58) Field of Search .................. 423/659; 554/170, 554/172, 173; 560/234; 568/679

(56) References Cited

U.S. PATENT DOCUMENTS 5,159,092 A * 10/1992 Leuteritz .................... 554/149
5,811,595 A 9/1998 Ellis

* cited by examiner

Primary Examiner—Wayne Langel
(74) Attorney, Agent, or Firm—Oblon, Spivak, McClelland, Maier & Neustadt, P.C.

(57) ABSTRACT

The invention relates to a process for conducting a chemical reaction characterized by an equilibrium in a reaction system designed as a loop reactor, said loop reactor comprising a reactor vessel (1), at least one loop connected to said reactor vessel (1) each by means of an outlet and an inlet, said loop comprising means (3) for pumping over a fluid reaction material, at least one he exchanger (4), optionally means (5) for feeding said reaction material into Me reactor vessel (1) and a separate gas loop (8) which is connected to the gas space of the reactor vessel (1) above the reaction mixture and has separate means for feeding a gas into the gas loop (8), for withdrawing gas from the gas loop (8) and/or for treating said gas circulating in the gas loop (8), said process comprising the steps of circulating and/or treating said gas in said gas loop (8), feeding said gas into the reactor vessel (1) for influencing the equilibrium of a reaction conducted in said reactor vessel (1) and being characterized by the equilibrium and, after influencing said equilibrium reaction conducted in said reactor vessel (1), exhausting said gas from said reactor vessel (1) into the gas loop (8).

27 Claims, 2 Drawing Sheets

METHOD FOR CARRYING OUT REACTIONS CHARACTERIZED BY AN EQUILIBRIUM

The present invention relates to a process for conducting reactions which are characterized by an equilibrium.

BACKGROUND OF THE INVENTION

1. Field of the Invention

Numerous chemical reactions including such reactions which are conducted in an industrial scale are characterized by the fact that a chemical equilibrium between educts and products is reached after a certain reaction time, which equilibrium may prevent the course of the chemical reaction from largely running to generate the desired products and, hence, may also prevent a high yield of the desired products from being obtained which high yield is important for the commercial value of said reaction.

2. Discussion of the Background

There are various attempts to solve such a problem by trying to influence the equilibrium of a chemical reaction in the desired direction. The basis for such attempts is the so-called mass action law ("Massenwirkungsgesetz") and the equilibrium constants which are dependent upon the reaction conditions and are defined by said law. Following the Le Chatelier principle, the chemical reaction runs into the desired direction, and there is established a new equilibrium which, due to a suitable influence, is shifted more to the side of the products.

Examples for such equilibrium reactions are the esterification of a carboxylic acid with an alcohol, resulting into the generation of an alklester of said carboxylic acid and water in accordance with the following equation:

$$R^1CO\text{—}OH + R^2O\text{—}H \rightleftharpoons R^1CO\text{—}OR^2 + H_2O \quad (1)$$

By continuously distilling off the water generated in the course of the reaction or by feeding the educts (carboxylic acid or alcohol) in excess, the equilibrium is shifted towards the right product) side of the above equation. In a comparable manner, carboxylic acid alkyl esters may be transesterified in the presence of alcohols and will set free the alcohol of the alkoxy group formerly bound in the starting ester:

$$R^3CO\text{—}OR^4 + R^5O\text{—}H \rightleftharpoons R^3CO\text{—}OR^5 + R^4O\text{—}H \quad (2)$$

A change of the reaction conditions (temperature, pressure) may contribute to influencing the state of the equilibrium, too. Practically, the above-mentioned measures for shifting the equilibrium to the product side do not always result into the desired success. Usually, this is due to the fact that a change of the reaction conditions is also accompanied by the generation of by-products which may raise problems not only in view of the product yield but also in view of the purity of the products. Separating undesired by-products from the desired products may strongly adversely affect the economic efficiency—particularly in a big-scale production. The presence of large amounts of educts or starting materials initially fed in excess often results into problems in connection with the purification of the desired product.

Physical equilibria may play a role, too, in conducting chemical reactions,

It is, for example, often required that certain reactions are conducted in (for example liquid) media which are free of oxygen or water or humidity, respectively, physically dissolved in the medium provided for a reaction. Usually, the air is exhausted from the vessel containing the medium in such a case, and the vessel is filled with an inert gas subsequently. Alternatively, the open system is rinsed or flushed, respectively, with an inert gas for a certain time. By such steps, the undesired gas or the humidity is stripped from the system; however, the inert filling gas or rinsing gas is lost. In addition, in plants for technically conducting chemical reactions, such steps cannot be carried out economically.

Solution equilibria of chemical substances in solutions may play in important role in conducting chemical reactions in a large scale, too. Subsequent to a chemical reaction, undesired by-products or educts may be dissolved in the reaction mixture. By-products as, for example, colouring agents or odoriferous substances or low-molecular by-products of a reaction randomly resulting into higher-molecular products or, in a similar manner, non-reacted educts remaining in the reaction mixture will have to be removed in costly purification steps which usually remarkably decrease the product yield.

The solution equilibria—in these cases: diffusion-determined solution equilibria—also include equilibria for dissolving gaseous reactants in liquid reaction systems. In the course of reactions including a gaseous and a liquid phase as, for example, hydrogenation reactions, oxidation reactions, nitrilation reactions, phosgenation reactions or alkoxylation reactions with alkylene oxides, the reaction rate, i. e. the rate by which an equilibrium is established which is shifted to the right (product) side as far as possible, is determined mainly by the amount of gas available in the liquid reaction medium for a contact with a dissolved reactant. For achieving practically useful reaction rates in usual reactions, the partial pressure of the reaction gas had to be relatively high in order to secure a sufficient gas concentration. This fact not only made a control of the reaction difficult sometimes, but, under usual conditions, also required the input of larger gas amounts than actually necessary for the reaction. Moreover, at the end of the reaction, it could not be avoided that a certain amount of unreacted gas had to be removed, since the partial pressure of said gas in the gas space was not sufficient for completely terminating the reaction of the gaseous reactant in said liquid reaction medium within an acceptable reaction time. The latter situation is not acceptable particularly in a case where the gas cannot be exhausted into the environment for safety reasons but has to be disposed expensively. This requirement, too, decreased the economic efficiency of many gas-liquid reactions considerably.

SUMMARY OF THE INVENTION

The invention had as an object to remove the above-described disadvantages of the prior art. In particular, there should be provided a process for conducting chemical reactions which are characterized by an equilibrium where the step of influencing the equilibrium, in favour of the desired course of the reaction, is possible to be taken in a simple and efficient way and by using means which do not put up physical or chemical resistance to a shift of the equilibrium.

It was a further object of the invention to provide such a process wherein the means for shifting the equilibrium is applicable as broadly as possible. Hence, the means should be inert to chemical reactions and, in view of economically conducting the process, should be cheap and available everywhere.

Further objects, advantages, and features of the process according to the invention may be learnt from the following description.

Surprisingly, it was found that it is possible to circulate, in a process of conducting chemical reactions which are characterized by an equilibrium, an inert gas in a separate gas loop, whereby it is possible to achieve the above-described objects.

The invention relates to a process for conducting a chemical reaction characterized by an equilibrium in a reaction system designed as a loop reactor, said loop reactor comprising a reactor vessel, at least one loop connected to said reactor vessel each by means of an outlet and an inlet, said loop comprising means for pumping over a fluid reaction material, at least one heat exchanger, optionally means for feeding said reaction material into the reactor vessel and a separate gas loop which is connected to the gas space of the reactor vessel above the reaction mixture and has separate means for feeding a gas into the gas loop, for withdrawing gas from the gas loop and/or for treating said gas circulating in the gas loop, said process comprising the steps of circulating and/or treating said gas in said gas loop, feeding said gas into the reactor vessel for influencing the equilibrium of a reaction conducted in said reactor vessel and being characterized by the equilibrium and, after influencing said equilibrium reaction conducted in said reactor vessel, exhausting said gas from said reactor vessel into the gas loop.

In the frame of the present invention, the term "equilibrium" is understood to include physical as well as chemical equilibria. From the following description, there may be derived particular examples according to the invention where the step of influencing the equilibrium is a step on influencing a physical equilibrium (e. g. a pure solution equilibrium), or where the step of influencing the equilibrium is a step of influencing a chemical equilibrium (e. g. of an esterification or of a transesterification). It may well be that, in a certain reaction system, both types of equilibria are simultaneously realized, and an influence thereon may be exerted simultaneously or one after the other.

The loop reactor used for the process according to the invention and enclosing the reaction system is a loop reactor known per se. Such reactors are usually employed as closed reaction vessels for conducting reactions of reactants dissolved in a liquid phase with other reactants dissolved in a liquid phase (including gaseous reactants). An example of such a reaction conducted in a loop reactor is disclosed in the document EP-A 0 419 419.

Figure 1:
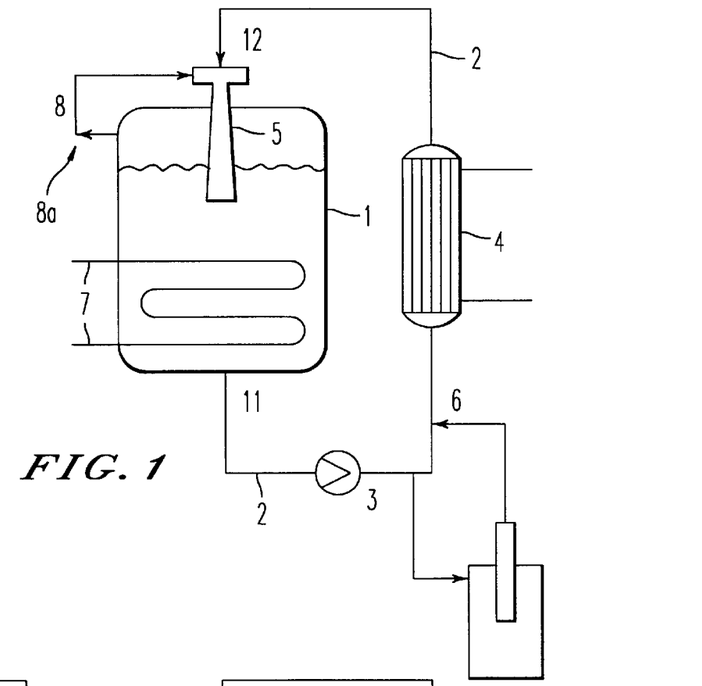
FIG. 1 shows a loop reactor.
Figure 2:
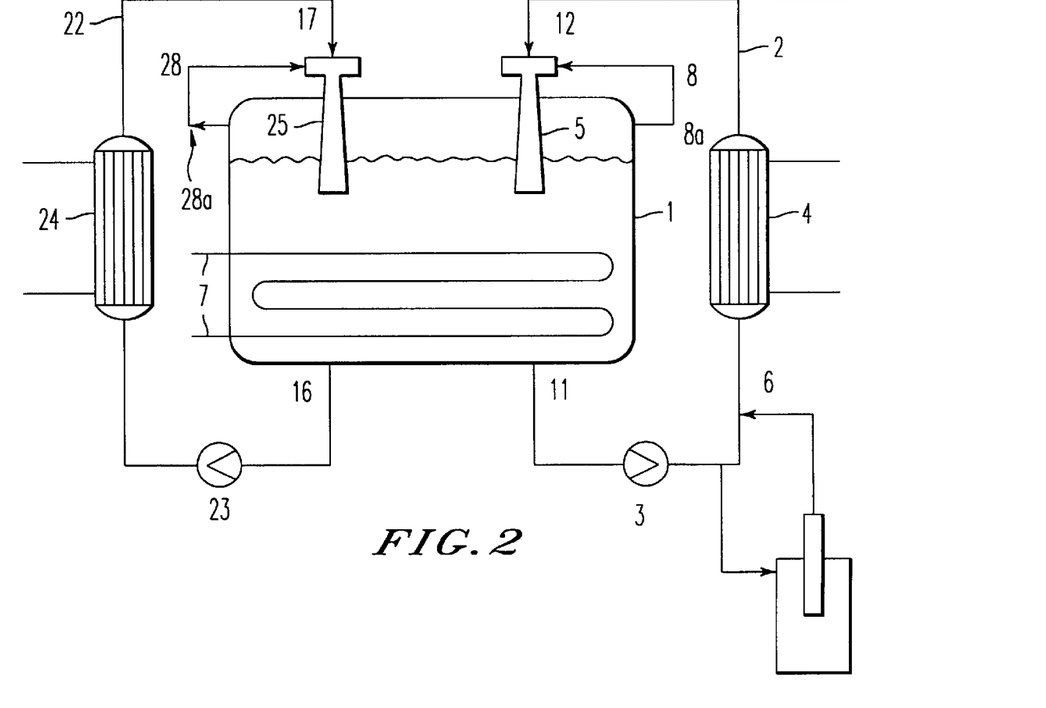
FIG. 2 shows a loop reactor having two loops.
Figure 3A:
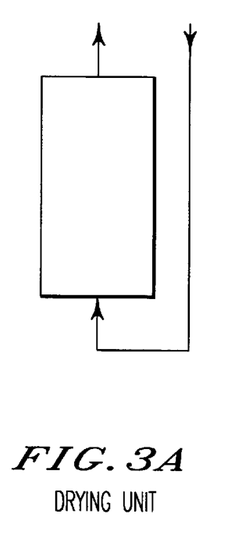
FIG. 3 shows separately disconnectable or separately connectable units.
Figure 3B:
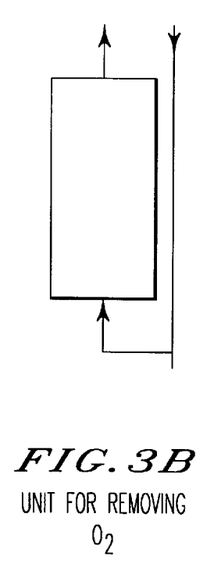
Figure 3C:
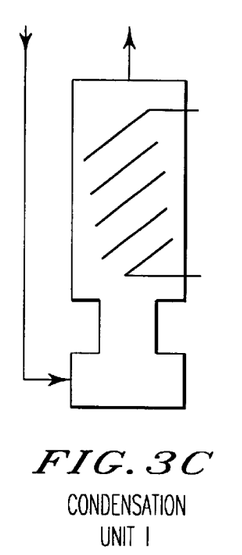
Figure 3D:
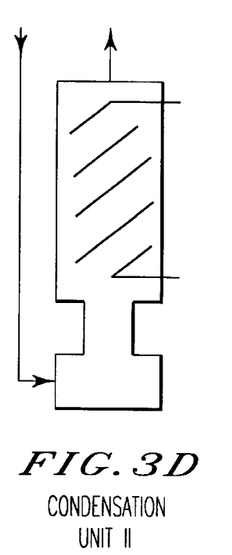

As can be seen from FIG. 1, such loop reactors usually comprise a reactor vessel 1 wherein a considerable portion, if not the major amount, of the reaction solution is contained. The reactor is provided with means 7 for heating and/or cooling of the reaction material, for example with a jacket for guiding a gas or a liquid which may serve for heating or cooling the reaction material, if this is necessary, Via each an outlet 11, 16 and an inlet 12, 17, there is connected to the reactor vessel 1 at least one loop 2, 22, through which the fluid reaction material may be conducted by force by means 3, 23 for transferring the fluid reaction material by pumping, Such means 3, 23 may be for example pumps. Usually, there is installed within the loop 2, 22 at least one heat exchanger 4, 24 which installation is preferred in the present invention. Dependent upon the reaction which is to be conducted within the loop reactor, the heat exchanger may have the function of a cooling device, on the one hand, or of a heating device, on the other hand, which cases are both comprised by the present invention. It is also possible that, in cases where two loops 2, 22 and, hence, two heat exchangers 4, 24, are installed, as shown in FIG. 2, at least one of them may serve as a cooling device, while the other one serves as the heating device.

At the inlet of the loop 2, 22 into the reactor vessel 1, there may be located a means for feeding the circulating reaction material into the reactor vessel 1. It may be that the loop 2, 22, at the inlet into the reactor vessel 1, feeds the reaction material into such a means or that the inlet itself is such a means for feeding the reaction material into the reactor vessel. Examples of such means are Venturi tubes or Venturi jets, jet nozzles or suction jet mixers, which provide a certain turbulence when feeding the reaction material into the reactor vessel 1 and thereby substantially improve the contact between the reactants (particularly in gas liquid reactions).

The loop reactor is provided with a separate gas loop 8, 28. The separate gas loop is in gas flow connection with the gas space of the reactor vessel 1 above the fluid reaction material and preferably has separate means for feeding gas into the gas loop 8, 28, separate means for removing gas from the gas loop 8, 28 and/or separate and/or separately disconnectable or separately connectable means for treating the gas within the gas loop 8, 28. In preferred embodiments of the invention, such a treatment of the gas may be an adsorptive treatment, a condensing treatment and a selective chemical (i. e. reactive) treatment of the gas; more preferred and, hence, advantageously useable are combinations of such treatments, since all conceivable possibilities of a treatment are available and may be selected.

The latter-mentioned means are shown in FIGS. 3A to 3D and may for example be separately disconnectable or separately connectable (for instance at the points 8a or 28a, respectively, in FIGS. 1 and 2) cartridges or units which are filled with per se known materials for removing $O_2$ (e. g. with a molecular sieve) or for removing humidity (e. g. with a desiccant as, for example Silicagel®), with an adsorbent (e. g. with activated charcoal, for example for removing low-molecular volatile components) or with a carrier which may bind selectively, by an active chemical reaction, reactive components and may thereby remove such components or convert them, respectively, into harmless, non-toxic substances and/or substances not harmful to the environment. Alternatively, such devices may, for example, also be separately disconnectable or separately connectable cartridges or units in the form of one or more than one condensers which may be connected in series and may serve for separating from the inert gas components which are entrained with the inert gas from the reaction system into the gas loop; the separation step, e. g. by condensation, may be carried out in one stage or in successive stages. In accordance with the invention, combinations of such units or means, respectively, are possible, for example a combination of a desiccant cartridge with one or more condenser(s), In accordance with the invention, in such a loop reactor an inert gas is conducted or treated, respectively, in a circulating manner in said gas loop 8, 28, is fed into the reactor vessel 1 for influencing the equilibrium reaction conducted in said reactor vessel 1 and is, after influencing the equilibrium of said reaction conducted in said reactor vessel 1, exhausted from said reactor vessel 1 into the gas loop 8, 28.

As the inert gas, there are suitable numerous gases. Basically, all gases are suitable which are inert in the specific reaction, i.e. do not react with one of the reactants in an undesired manner. In the sense of this general definition of an inert gas, a gas may be used for a specific equilibrium reaction which does not react with one of the reactants in an undesired manner under the conditions given, but which may not be inert in other reactions or under other reaction conditions. However, in the sense of a broadest-possible suitability, there are preferred as the inert gases, in accordance with the present invention, nitrogen ($N_2$), argon (Ar), carbon dioxide ($CO_2$) water ($H_2O$) and other inert substances which are gaseous under the reaction conditions. There may be used mixtures of the above-mentioned gases with one or more than one other inert gases, too, in accordance with the present invention. It is one of the advantages of the present invention that there may be used in the closed system of a loop reactor such inert gases, too, in an industrial scale which, due to cost reasons, usually cannot be used since the reaction system has to be filled with the desired inert gas only once, and said inert gas is circulated in the gas loop 8, 28 and in the gas space above the fluid reaction medium and is optionally cleaned and re-fed into the gas loop and circulated again. Thereby, a loss of (even expensive) inert gases may be avoided. Preferably, nitrogen is used as the inert gas, since nitrogen is available everywhere, may be produced at low costs and is effective with respect to its properties to influence equilibria.

The inert gas is circulated in the gas loop 8, 28 and/or may be treated. A circulation of the inert gas in the gas loop 8, 28 may also serve to conditioning the inert gas for the subsequent step of influencing the equilibrium of a chemical reaction conducted in the reaction system. In preferred embodiments of the process according to the invention, such a conditioning step may consist of steps of heating, cooling, removing from the inert gas undesired components (e. g. humidity=drying; oxygen or air, respectively= deoxygenation; other gaseous contaminants=cleaning) or adding to said inert gas desired gaseous substance. The latter step may be advantageous, for example, in a case where the desired gaseous substance should be charged into the fluid reaction system with the aim of better distributing said gaseous substance despite a reduction of its partial pressure within said system, in order to influence the equilibrium of the chemical reaction in the sense of better contacting said gaseous substance with the other reactant(s). Another advantageous embodiment of adding a desired gaseous substance to the inert gas is the controlled provision of a reducing or oxidizing environment in the course of a reaction otherwise not influenced in an oxidative or reductive manner. This may, for example, be desired for the purpose of preventing side reactions.

In accordance with the invention, the inert gas is fed from the separate gas loop 8, 28 where it was conducted and/or treated into the reactor vessel 1 in order to influence the equilibrium of the chemical reaction or to shift the equilibrium into the desired direction, respectively. There are possible different types of influencing or shifting the equilibrium, which types are explained in detail hereinafter. The inert gas may be fed into the gas space above the fluid reaction medium or may be fed directly into the fluid reaction medium. In the later case, the inert gas may be fed, for example, via the means 5, 25 for feeding the fluid reaction medium into the reactor vessel 1. There are possible, however, other ways for feeding the inert gas as, for example, a way of feeding the inert gas directly into the loop 2, 22 (or at any other location) into the fluid reaction material. The step of feeding may be selected in a skilled manner by a person familiar with this field of the art In a preferred embodiment of the process according to the invention, the inert gas influences the equilibrium of a chemical reaction within the reactor vessel 1 in such a manner that the inert gas cleans the reaction mixture from a gas dissolved therein (or from undesired low-molecular components which usually can be removed by a separate carrier distillation only) and withdraws said gas from the reaction mixture. The influence may be exerted in accordance with the following equilibrium reaction:

Such influence may result into the creation of a reaction mixture stripped of undesired gaseous components. This may be necessary in cases where the reaction mixture must not contain any oxygen which interferes with the reaction, directs the reaction into an undesired direction or influences one of the reactants involved into the reaction with respect to its effects in said reaction. Such a step of removing the oxygen from a reaction medium is conducted, for example, before a reaction in order to protect the reaction products against oxidative decomposition (e. g. during the condensation of highly unsaturated fatty acids or during the esterification of highly unsaturated fatty acids), for avoiding the generation of low-molecular by-products (e. g. during polymerization reactions) or for protecting catalysts against a loss of activity (e. g. for protecting phosphorous acid against an oxidation to phosphoric acid during the esterification of sorbitol to sorbitane esters). In order to deoxidize the reaction mixture, the inert gas as, for example, nitrogen which is conducted in the gas loop 8, 28 is fed into the fluid reaction material, preferably directly into the reaction material. The inert gas is bubbling through the reaction material, preferably (but not necessarily) with high turbulence, for example in the form of a plurality of fine bubbles, and superimposes the above equilibrium (3) by the following equilibrium (4):

The gas "displaced" from the solution by the nitrogen charged into the vessel is discharged by an excess of nitrogen from the reaction mixture and, subsequently, from the reactor vessel 1, flows into the gas loop 8, 28 and is separated there from the inert gas in the course of the treatment of the inert gas. Such a treatment of the mixture of inert gas and oxygen in the gas loop 8, 28 may be conducted in accordance with processes known to a skilled person for such a treatment. To give just one example: Such a treatment may be a treatment of the mixture of the inert gas and oxygen by means of a molecular sieve selectively removing the oxygen. The molecular sieve is preferably (but not necessarily) filled into a cartridge through which the mixed gas is forced to flow. Other methods of treatment are conceivable for separating the oxygen from the inert gas. After the treatment step, the inert gas is available again for another cycle of removing of oxygen. There are no losses of the inert gas. Of course, the oxygen may also be swept away by the use of nitrogen in an open system without recycling the nitrogen into the loop. However, this embodiment is less preferred than the above-described embodiment.

It is another example of the same principle to condition the reaction mixture by the controlled addition of low amounts of a reactive gas in a step preceding the reaction in such a manner that the generation of by-products is prevented in the subsequent reaction. For example, there may be reduced oxidatively generated groups (hydroperoxides, peroxides and other intermediate products) by a pretreatment with $H_2$ before the reaction of unsaturated raw fatty acids.

In the same manner, the inert gas may be used to remove humidity from the reaction mixture provided for the reaction before the start of the reaction in the reactor vessel. In the course of influencing the solution equilibrium by the inert gas, the inert gas as, for example, nitrogen, is charged into the reaction mixture in the same way as described above, preferably in a turbulent manner, displaces the water dissolved from the reaction mixture and discharges the water into the gas space above the reaction mixture or into the gas loop 8, 28, respectively. In the gas loop, the inert gas is "dried" in a per se known manner, i. e. the water is separated. This is carried out in the gas loop in a per se known manner. An example for the process of drying which is particularly preferred in a case where low amounts of water (humidity) are discharged by the inert gas is the step of allowing the inert gas to pass a cartridge filled with a usual desiccant, e. g. a cartridge filled with Silicagel®, If larger amounts of water are present, there are preferred other process (which are known to a skilled person, too), for example the step of freezing out the water in a condenser integrated into the gas loop. After the step of "drying", the inert gas is available for another drying cycle. Of course, the humidity (the water) may also be swept away by the use of nitrogen in an open system without recycling the nitrogen into the loop. However, this embodiment is less preferred than the above-described embodiment.

It goes without saying that, in the process according to the invention, it is possible in the treatment of gases in the gas loop to connect in series units for condensing, units for adsorbing, units for drying, units for actively reacting reaction components etc. in an arbitray (but nevertheless meaningful) order and combination. By such a combining step, the degree of separation of the components to be separated by the treatment in the gas loop may be enhanced, which enhancement improved the efficiency of the process. It is even more preferred to separate, by condensation, large amounts of volatile components removed from the equilibrium reaction and discharged into the gas loop and, thereafter, separate small (remaining) amounts by adsorption or by a chemical reaction.

The same process as described above is applied, if low-molecular contacts present already in the raw starting materials and generated by aging and/or decomposition are to be removed from the reaction system. Such components usually have to be removed, in a troublesome procedure, by a carrier distillation. The process of the present invention allows a more simple and carefully removal of such contaminants already in the system which is used for the subsequent reaction.

An influence of the inert gas on solution equilibria is exerted, in another preferred embodiment of the invention, in cases where an equilibrium reaction with a gas as one of the reactants is shifted towards the product side by adding an excess of said gas. In accordance with the above equation (4), the non-reacted excess of gas may be discharged from the reaction mixture. Thereby, a rapid, efficient and complete removal of an excess of the gaseous reactant may be achieved already in the reactor vessel. This is particularly important in the industrial area, for example when carrying out batch processes, especially when carrying out reactions with environmentally relevant, toxic or highly reactive gases. Examples of such processes are phosgenations, carbonylation reactions or alkylation reactions. The excess reactants discharged by the inert gas (e. g. $COCl_2$, CO or RCl) are separated from the inert gas in a per se known manner, for example by a chemical reaction or by adsorption or by condensation.

In another preferred embodiment of the present process, the inert gas exerts an influence on a reaction characterized by an equilibrium and conducted in the reactor vessel 1 in such a way that the inert gas incorporates a reactant into the reaction mixture. This may lead to a positive result in all cases where gaseous reactants have to be incorporated into a reaction mixture and either an accelerating or decelerating control of the reaction is desired;

or a certain (e. g. a low) partial pressure of a gaseous reactant is desired (optionally with view to controlling the reaction);

an equilibrium is to be shifted, gently and by avoiding a large excess of one gaseous reactant, to the product side.

The latter (relatively frequent) influence on an equilibrium is necessary, for example, in chemical reactions which (of course not desired) start only after a certain incubation period. An incubation period is surprisingly shortened or rendered harmless, in some cases even avoided, if the process of the invention is applied wherein the equilibrium is influenced by the action of an inert gas.

Examples of the above reactions may be all equilibrium reactions running with the participation of a gas on the educt side, e. g. hydrogenation reactions, oxidation reactions, alkoxylation reactions, nitriliation reactions, phosgenation reactions, halogenation reactions, alkylation reactions, sulfation reactions, sulfatation reactions etc. In the course of such reactions, it may be desirable to improve the contact between the reactant gas and the other reactant(s) already dissolved in the reaction mixture by the combined addition of the reactant gas and the inert gas, to avoid, by "diluting" the reactant gas, a too rapid reaction of highly reactive gaseous reactants and to prevent thereby side-reactions at a too high temperature and a too high concentration of the reactant gas, to avoid a too high excess of the reactant gas for economical or reaction-technical reasons or to employ harmful or dangerous or expensive reaction gases in a reaction only at low partial pressures, but nevertheless in an efficient manner. These objects are achieved by charging the reactant gas in combination with an inert gas in accordance with the invention Substantial advantages may be achieved insofar as the thermal, kinetic and thermodynamic parameters of the reaction are improved. In addition, side-reactions are prevented or largely suppressed by the participation of the reaction gas by "diluting" said reaction gas with the inert gas, while the reactivity with respect to the liquid phase is maintained. Thus, the generation of decomposition products or is avoidable in a similar way as condensation reactions or rearrangement reactions (inactivation).

It is a particularly preferred embodiment of the invention that the gaseous reactant charged with the inert gas is present in an amount corresponding to a partial pressure condition on the progressive termination of the reaction. This is of importance, for example, in cases where an equilibrium reaction conducted with the participation of a gaseous reactant is not terminated abruptly, but is intended to come to an end after the termination of the step of charging or adding, respectively, the gaseous reactant with more or less completely reacting off the gas as, for example, in alkoxylation reactions. In the prior art, usually a certain amount of gas (alkylene oxide) remained unreacted in the reaction mixture or in the gas space of the loop reactor, if it was intended not to allow the reaction to continue for an unecomically extended time period. In accordance with the invention, by using an inert gas as $N_2$, a completion of the reaction can be achieved, even if the partial pressure of the gaseous reactant is reduced at the end of the reaction, and there is no need to exhaust or pump out the reaction gas. Thereby, not only are avoided separate measures for preventing a threat of the environment (for security reasons, for health reasons; e. g. costly apparatus for gas purification), but there is also allowed an economic conduction of the process, accompanied by a proper utilization of resources.

A broad application in the sense of influencing equilibrium reactions results from the embodiment of the present invention where the inert gas exerts an influence on the reaction characterized by an equilibrium in the reactor vessel 1 in such a manner that the inert gas withdraws a volatile reactant from the reaction mixture. It is particularly preferred that the removal of the volatile reactant by the inert gas occurs during the course of the reaction and that the reactant withdrawn from the reaction mixture by the inert gas is a product of the reaction characterized by an equilibrium which product is generated during said reaction. Thus, in the course of, for example, the esterification reaction represented by the above equation (1), the volatile reaction product water may be discharged from the equilibrium reaction mixture by an inert gas. Thereby, the equilibrium of the esterification reaction is shifted efficiently towards the product side without any thermal stress and without employing an excess of any educt. The water is discharged in a simple manner from the reaction mixture and is conducted with the inert gas into the gas loop. In the gas loop, it may be separated from the inert gas in a per se known manner without problems. Thereafter, the inert gas is available again for another dewatering cycle. There are no losses of the inert gas.

In an analogue manner, the alcohol $R^4O$—H generated as a product in the course of the transesterification reaction represented by the above equation (2) may be discharged from the reaction mixture as a volatile product. If it is desired, the equilibrium of the transesterification reaction may thus be shifted to the product side. The separation of the alcohol from the inert gas in the course of the treatment of the inert gas in the gas loop 8, 28 is without problems (and known per se) in the some manner as the separation of water from the inert gas after the esterification reaction. Finally, pure inert gas is recovered for another cycle, The equilibrium of a directed transesterification reaction according to the equation (5)

$$R^6CO\text{—}OR^7+R^8CO\text{—}OR^9 \rightleftharpoons R^6CO\text{—}OR^9(\uparrow)+R_8CO\text{—}OR^7 \quad (5)$$

may be shifted to the product side of the above equation, too, by adding an inert gas in the course of the reaction. This is possible particularly in cases where the reaction product $R^6CO$—$OR^9$ is volatile due to the length of the alkyl residues $R^6$ and $R^9$ and, hence, may be discharged by the inert gas. In the technical area, this plays a role, for example, for transesterifying coconut oil for enhancing its melting point. In such a reaction, esters of relatively long chain fatty acids are reacted with coconut oil and, thereby, long chain acyl residues are inserted into the oil. Naturally, shorter chain fatty acids in the form of their esters become free. The equilibrium of said reaction may be shifted to the product side by discharging the relatively short chain esters. The inert gas entrains the esters of said relatively short chain fatty acids and discharges them into the gas loop, where they are separated in the course of the treatment of the inenrt gas. Subsequently, the inert as is available for another cycle.

Basically, the same reaction is carried out in the course of the transesterification of triglycerides with non-volatile fatty acids or in the course of the transesterification of polyalcohols with methyl esters. During such reactions, too, the equilibrium may be shifted towards the product side, if the fatty acids generated or the methanol generated is discharged, respectively.

In another preferred embodiment of the process according to the invention, the inert gas influences the reaction equilibrium by withdrawing a volatile reactant in such a way that the influence is exerted after completion of the reaction and either the reactant withdrawn from the reaction mixture by the inert gas is an excessively employed starting material of the reaction characterized by an equilibrium or the reactant withdrawn from the reaction mixture by the inert gas is a product of the reaction characterized by an equilibrium which product is generated in the course of the reaction or, alternatively, one of the reactants is an excessively employed starting material of the reaction characterized by an equilibrium and another one is a product of the reaction characterized by an equilibrium which product is generated in the course of the reaction.

An example for the first case (the reactant withdrawn from the reaction mixture by the inert gas is an excessively employed starting material of the reaction) is the deodorization of the reaction mixture after the reaction of glycerol with (removable under the process conditions and optionally short chain) fatty acid to triglycerides according to the equation (6)

$$\text{Glycerol}+3R^{10}CO\text{—}OH \rightleftharpoons \text{triglyceride}+3H_2O \quad (6)$$

Since even small amounts of unreacted, severely smelling fatty acid adversely affect the smell and taste of the product, a deodorization of the product mixture after completion of the reaction is essential. From the product mixture, the relatively volatile fatty acid may easily be removed by employing an inert gas. By such a step, a deodorization of the product in an industrial scale can be carried out rapidly and efficiently without additional steps. In the same way, an excess of glycerol, if an excess amount thereof is employed, may be removed after a complete reaction of the fatty acid. Optionally, excess starting materials may be recycled into the reaction loop.

Examples for the second case (the reactant withdrawn from the reaction mixture by the inert gas is a product of the reaction characterized by an equilibrium, said product being generated in the course of said reaction) are the esterification conducted according to the above equation (1) or the transesterification conducted according to the above equation (2). By means of a carrier gas like nitrogen, the desired ester ($R^1CO$—$OR^2$ in the case of reaction (1); $R^3CO$—$OR^5$ in the case of reaction (2)), if it is volatile, is separated from the reaction mixture. Thereby, a product pure and free from by-products and/or starting materials is obtained in one step. When treating the inert gas in a per se known manner, the product is completely separated from the inert gas, and finally the inert gas clean and suitable for another separation cycle is obtained.

Examples for the third case (one of the reactants is an excessively employed starting material of the reaction characterized by an equilibrium and another one is a product of the reaction characterized by an equilibrium which product is generated in the course of said reaction) are the concentration of products of a certain degree of alkoxylation during the alkoxylation of, for example, fatty alcohols and the purification of the triglycerides generated by the reaction of glycerol with, for example, fatty acid methyl esters. In the alkoxylation reaction, the relatively volatile reactants fatty alcohol (educt) and low alkoxylated fatty alcohols (products) may be separated from the higher alkoxylated fatty alcohols (products) after the completion of the reaction by means of an influence of the inert gas on the solution equilibrium. Thereby, the desired products are obtained in relatively high yield and purity. The substances withdrawn by means of the inert gas are easily separated in the inert gas treatment step. In a comparable manner, there may be separated in the triglyceride preparation after the completion of the reaction fatty acid methyl ester starting material (educt) as well as methanol (product), optionally partial esters of glycerol (monoesters or diesters) as by-products or methyl ethers as by-products as the more volatile components of the reaction mixture.

In a particularly preferred embodiment of the reaction, the above principle is applied to the deodorization of nutrient fats or oils, respectively. Such fats and oils were treated in the prior art in cascades under vacuum (about 1.33 mbar) at temperatures of up to 270° C. in a reverse flow against water vapor in order to remove undesired by-products having a molecular weight below that of the fats or oils, respectively. Simultaneously, there was carried out in part a decomposition of coloring bodies and epoxides or hydroperoxides, respectively, resulting from the steps of chemical bleaching or adsorptive bleaching by means of bleaching earths and their subsequent removal. In the process according to the invention, the removal of the by-products, i. e. a step of bleaching and a subsequent step of deodorization, are carried out in the loop reactor by feeding $H_2$ and $N_2$, optionally in the presence of a catalyst, and thereafter by feeding $N_2$ for discharging the by-products into the gas loop (optionally with co-feeding of water vapor in order to improve the separation effect). The nitrogen discharges the easily volatile odoriphores into the gas loop, where they are separated from the carrier gas in a manner known to a skilled person, e. g. by adsorptive means by inserting a cartridge containing an adsorbent. Such a deodorization is recommended particularly after the industrial scale hydrogenation of nutrient fats and oils, which may be carried out advantageously in the present loop reactor, too. In such a case, the process of the invention affords the advantages described in the present description. It is particularly advantageous that the presently employed plants will have to be retrofitted only with the gas loop installed outside the reactor system.

As described, the latter-mentioned reactions are usually carried out after completion of the main reaction, in many cases due to the fact that the amount of educt present in the reaction is needed in order not to undesirably shift the equilibrium of the reaction towards the educts. In single cases, it is, however, possible to carry out the separation of the starting materials an/or the separation of the generated reaction products already in the course of the process, if advantages are achieved for the status of the equilibrium or for other features of the reaction.

It is another embodiment preferred in the frame of the process of the invention to provide a certain gaseous atmosphere in the space above the reaction mixture and, thereby, also in the reaction mixture by means of an inert gas and to promote the course of the reaction by such a step. This may be of importance when treating natural fats before chemical reactions are carried out. Reducible groups present in such fats due to the storing or transport (epoxide groups, hydroperoxide groups) may be reduced by $H_2$ as a pretreatment. For this purpose, an inert gas as the carrier or vehicle is used for influencing the solution and reaction equilibria. The efficiency of the reaction is remarkably improved, and subsequent reactions are carried out with obtaining the desired fatty product in a high yield.

The adjustment of reducing conditions is desired, too, in the esterification of sorbitol to sorbitan esters, For this reaction (substantially following equation (1)), there are selected catalysts (phosphorous acid or its salts) which have reducing properties in order to prevent the generation of chromophore by-products which impair the product quality. If usual esterification catalysts are employed under reducing conditions (addition of $H_2$ to the reaction mixture by means of the inert carrier gas $N_2$), the generation of by-products is largely suppressed, particularly of chromophore and odoriphore substances.

In all examples mentioned above, the respective equilibrium may be shifted in a simple and efficient way in favour of the desired course of the reaction by the influence of the inert gas. The inert gas does not participate in the reaction and may be recovered completely by easy process steps. It is not used up which fact makes it possible to employ expensive inert gases. There are no physical or chemical forces offering resistance to a shift of the respective equilibrium. The desired reaction products are obtained in high yield and high purity. Furthermore, in systems employing a catalyst, the catalyst amount may be drastically reduced, partly to 1/10 of the amount employed in the prior art, which fact affords not only remarkable cost savings with respect to the catalyst consumption, but also substantially reduces the problems involved in a separation of the catalyst.

In the following, the invention is illustrated by means of the following examples without being restricted to these examples.

EXAMPLES

Example 1

Preparation of a Caprylic Acid—Capric Acid Triglyceride from the Corresponding Methyl Esters Into a loop reactor according to the enclosed FIG. 1A having a reactor vessel content of 65 liters (1) and comprising a gas loop into which connectable units for removing oxygen, for drying and for reacting reactive components of the reaction as well as for condensing were integrated and which contained in the liquid circulation loop an optionally connectable filtration unit 6, there were charged 40 kg (231 moles) of a mixture of caprylic acid methyl ester and capric acid methyl ester (weight parts $C_8$; $C_{10} \approx 1:1$) and 6.07 kg (66 moles) of glycerol. The reactor was flushed and filled with $N_2$, and the temperature was adjusted to 60° C.

During a cleaning step of 15 minutes and circulating the liquid phase by pumping with a circulation capability of 3.6 m³/h, the gas loop was operated. Successively, the drying unit and then the unit for removing oxygen were connected to the loop. The flow rate at the outlet of the suction jet mixer was in the order of 17 m/s.

After finishing the flushing step, the gas loop was connected to the condensation unit, while the drying unit and the unit for removing oxygen were disconnected. 0.46 kg of a 50% potassium methylate (soluble in methanol, inertized) were added as a transesterification catalyst. The temperature was increased to the reaction temperature of 100° C.

The transesterification was conducted for a time period of 30 min at 100° C. During this time, the methanol generated was continuously discharged into the gas loop and was condensed in the condensation unit at 0° C.

As soon as the discharge of MeOH ceased, the reactor was charged with 800 g of citric acid in crystalline form. After 10 min of circulating the citric acid in the reaction mixture, it was removed as potassium citrate via the filtration unit connectable to the liquid circulation loop.

The reaction mixture consisting of the triglyceride obtained, excessive methyl esters and lower molecular weight contaminants, non-reacted educts and by-products generated in the course of the reaction was heated to 200° C. By operating the gas loop; all components mentioned above having a lower molecular weight than the triglyceride were discharged into the gas loop, with the exception of the desired triglyceride, and were singly separated from the nitrogen gas by condensing them in the condensation unit.

The triglyceride obtained after cooling (32 kg) was free of by-products, as could be seen from a thin layer chromatography test, particularly free of methyl ester, of partial glycerides and of free fatty acids.

Comparative Example 1 and Example 2

Preparation of Sorbitane Esters under Reducing Conditions

Into the loop reactor described in Example 1, there were charged 17.5 kg of sorbitol (70% in $H_2O$) and 27.7 kg of oleic acid together with 0.3 kg of NaOH (50% in $H_2O$) and 0.13 kg of crystalline phosphorous acid. After flushing and inertizing with pure nitrogen, the reaction was conducted for a time period of 1 h at a temperature of 180° C. and thereafter for a time period of 2 h at a temperature of 240° C. In the course of the reaction, the solution water and the reaction water were discharged into the gas loop by pure nitrogen, which gas loop had been connected to two condensers operated at different temperatures. In the first condenser (110° C.), the discharged fatty acid was separated; in the second condenser (10° C.), the water was separated. The fatty acid recovered was recycled into the reactor 1 h before the completion of the reaction. The sorbitane ester obtained had a hydroxyl number of 205 to 208 and a color value (Hess-Ives) of 10.

The above-described reaction was repeated with the exception that hydrogen (partial pressure: 0.1 bar) was added to the nitrogen circulated in the gas loop. The sorbitan ester obtained had a hydroxyl number of 205 to 208 and a color value (Hess-Ives) of 5.

Example 3 and Comparative Example 2

Preparation of Coconut Fatty Acid Dimethyl Aminopropyl Amide (Removal of Oxygen)

Into the loop reactor described in Example 1, there were charged 33 kg of coconut fat and 18 kg of dimethyl aminopropyl amine. At 90° C., the oxygen was removed from the mixture via the gas loop by flushing with nitrogen. The subsequent reaction to coconut fatty acid dimethyl aminopropyl amide was conducted at a temperature of 180° C. for a time of 1 h without employing the condensation unit. The raw aide obtained had a color number clearly below 100 Hazen.

The above reaction was repeated, with the exception that the oxygen was not removed from the educt mixture, The product had a color number of about 500 Hazen.

Example 4

Drying of a Reaction Educt Mixture

In the loop reactor described in Example 1, 40 kg of $C_{12/14}$ fatty alcohol and 24 g of KOH (50% in $H_2O$) were circulated at a temperature of 140° C. for a time of 30 min with circulation of $N_2$ in the gas loop. The nitrogen was conducted through a condensation unit connected to the gas loop and thereafter through a drying unit connected in series. The water content before the treatment was 0.1%. By the drying step, the water content could be reduced to <0.001%. The low water content obtained allowed to drastically reduce the content of polyethylene glycol in ethoxylates prepared with such a dry educt mixture.

Example 5

Preparation of an Ethoxylate of a $C_{12/14}$ Fatty Alcohol with 2 Moles of Ethylene Oxide In the loop reactor described in Example 1, 40 kg of a mixture of lauryl alcohol/myristyl alcohol were inertized. Thereafter, there were added 24 g of KOH (50% in $H_2O$). The mixture was dried by circulating while flushing with nitrogen, as described in Example 4. Thereafter, the reaction was conducted with continuously feeding ethylene oxide (8.8 kg in total) while maintaining a reaction temperature of 160° C. The reaction was terminated in such a way that the supply of ethylene oxide was finished, but the ethylene oxide present in the system was completely reacted. Thereafter, the catalyst was destroyed by the addition of acetic acid.

Subsequently, the temperature of the reaction mixture was increased to 230° C. At such a temperature and within a time period of 1 h, fatty alcohol and singly ethoxylated fatty alcohol were discharged from the reaction mixture by circulated nitrogen, while simultaneously charging water vapor before the suction jet mixer, and were separated from the nitrogen by condensation in the condensation unit.

Before the separation of educts and by-products, the reaction mixture had a content of $C_{12/14}$ fatty alcohol of 12% by weight and a content of singly ethoxylated adduct (ROH+1 EO) of 10% by weight. However, after the separation of the educts and by-products, the content of $C_{12/14}$ fatty alcohol was reduced to 3% by weight, and the content of singly ethoxylated adduct (ROH+1 EO) was reduced to 7% by weight. Such a decrease of the content of lipophilic components in the reaction product results into a substantially enhanced water solubility.

What is claimed is:

1. A process for conducting an equilibrium chemical reaction including a volatile reactant in a loop reactor, said loop reactor comprising:

a reactor vessel;

at least one loop connected to said reactor vessel by an outlet and an inlet; wherein said loop comprises means for pumping a fluid reaction material, at least one heat exchanger, optionally means for feeding said fluid reaction material into said reactor vessel; and a closed gas loop separately connected to the gas space of the reactor vessel above said fluid reaction material;

wherein said gas loop has at least one means for feeding at least one volatile material into said gas loop, for withdrawing at least one volatile material from the gas loop and for treating at least one volatile material circulating in the gas loop;

said process comprising the steps of:
circulating or treating or concomitantly circulating and treating an inert gas as one of the at least one volatile material in said gas loop of said loop reactor;
feeding said at least one volatile material from the gas loop into the reactor vessel of said loop reactor;
removing said at least one volatile material from said reactor vessel of said loop reactor into said gas loop; and repeating the sequence of circulating/treating, feeding and removing said at least one volatile material, thereby influencing the equilibrium of said chemical reaction; wherein a volatile reactant as another volatile material to be fed to or removed from the loop reactor is supplied or removed exclusively via the gas loop.

2. The process according to claim 1, wherein said volatile reactant is selected from the group consisting of a volatile component of the starting reaction mixture interfering with a reaction to be conducted, a volatile reactant to be added to the starting reaction mixture, an excessively employed starting material, a reaction product of said reaction conducted, and a combination thereof.

3. The process according to claim 2, wherein said volatile component of the starting reaction mixture interfering with a reaction to be conducted is a gas contained in the starting material or in the solvent.

4. The process according to claim 3, wherein said gas is oxygen.

5. The process according to claim 2, wherein said volatile component of the starting reaction mixture interfering with a reaction to be conducted is a volatile liquid contained in the starting material or in the solvent.

6. The process according to claim 5, wherein said volatile liquid is water.

7. The process according to claim 2, wherein said volatile reactant to be added to the starting reaction mixture is a gaseous reactant or a volatile liquid reactant to be reacted.

8. The process according to claim 2, wherein said excessively employed starting material is a gaseous reactant or a volatile liquid reactant to be reacted.

9. The process according to claim 2, wherein said reaction product of said reaction conducted is a final reaction product or a by-product of said reaction.

10. The process according to claim 1, wherein said inert gas is charged into said reaction mixture and wherein said volatile reactant is a gas.

11. The process according to claim 1, wherein said inert gas is charged into said reaction mixture and discharges oxygen or air from the reaction mixture, which discharged oxygen or air is separated from the inert gas circulated in the gas loop in said means for treating the volatile material circulating in the gas loop.

12. The process according to claim 1, wherein said inert gas is charged into said reaction mixture and discharges water or humidity from the reaction mixture, which discharged water or humidity is separated from the inert gas circulated in the gas loop in said means for treating the volatile material circulating in the gas loop.

13. The process according to claim 1, wherein said inert gas is charged into said reaction mixture and discharges an excessively employed starting material from the reaction mixture, which discharged excessively employed starting material is separated from the inert gas circulated in the gas loop in said means for treating the volatile material circulating in the gas loop.

14. The process according to claim 1, wherein said inert gas is charged into said reaction mixture and discharges a reaction product of said reaction conducted from the reaction mixture, which discharged reaction product of said reaction conducted is separated from the inert gas circulated in the gas loop in said means for treating the volatile material circulating in the gas loop.

15. The process according to claim 14, wherein said reaction product of said reaction conducted is a by-product.

16. The process according to claim 14, wherein said reaction product of said reaction conducted is a product of a polymerization reaction having a lower molecular weight than the main product.

17. The process according to claim 1, wherein said inert gas is charged into said reaction mixture after being supplied with a gaseous reactant and charges said gaseous reactant into the reaction mixture.

18. The process according to claim 17, wherein said gaseous reactant has a low partial pressure.

19. The process according to claim 17, wherein said gaseous reactant has a low partial pressure conditional on a ceasing of the reaction.

20. The process according to claim 1, wherein said inert gas is charged in a turbulent manner into the reaction mixture.

21. The process according to claim 1, wherein said inert gas is conditioned in the gas loop before being fed into the reaction mixture.

22. The process according to claim 1, wherein the inert gas and a volatile reactant are withdrawn from the gas space above the reaction mixture into the gas loop, wherein the inert gas withdraws said volatile reactant from said reaction mixture in the reactor vessel;

said inert gas is cleaned of said volatile reactant; and said inert gas is circulated in the gas loop and is re-fed into the reactor vessel.

23. The process according to claim 22, wherein the withdrawal of the volatile reactant is conducted during the course of the reaction or after a completion of the reaction; and wherein said volatile reactant is separated from said inert gas in the gas loop; and wherein said volatile reactant is an excessively supplied educt of said equilibrium reaction.

24. The process according to claim 22, wherein the withdrawal of the volatile reactant is conducted during the course of the reaction or after a completion of the reaction; and wherein said volatile reactant is separated from said inert gas in the gas loop; and wherein said volatile reactant is a product or by-product of said equilibrium reaction or a combination thereof.

25. The process according to claim 1, wherein the inert gas is selected from the group consisting of nitrogen ($N_2$), argon (Ar), $CO_2$, $H_2O$ and a mixture thereof.

26. The process according to claim 1, wherein the inert gas is a mixture containing nitrogen ($N_2$).

27. The process according to claim 1, wherein said step of treating said inert gas in said gas loop is carried out by condensation, freezing, adsorption, drying, treatment with a molecular sieve or a combination thereof.

* * * * *

UNITED STATES PATENT AND TRADEMARK OFFICE
CERTIFICATE OF CORRECTION

PATENT NO.    : 6,342,199 B1
DATED         : January 29, 2002
INVENTOR(S)   : Ellis It is certified that error appears in the above-identified patent and that said Letters Patent is hereby corrected as shown below:

<u>Title page,</u>
Item [76], the Inventor should read:
[76]  Inventor: Vincent Simon Ellis, Schutterslaan 11,
               B-3078 Everberg (BE)

Signed and Sealed this

Eleventh Day of June, 2002

*Attest:*

JAMES E. ROGAN
*Attesting Officer*     *Director of the United States Patent and Trademark Office*